United States Patent [19]

Dubroeucq et al.

[11] 4,435,393
[45] Mar. 6, 1984

[54] DERIVATIVES OF 10-(1-AZABICYCLO(2.2.2)OCT-3-YL)-N,N DIMETHYL-10H-PHENOTHIAZINE-2-SULFONAMIDE AS MEDICAMENTS

[75] Inventors: Marie-Christine Dubroeucq, Enghien-les-Bains; Jean E. M. A. Rataud, Paris, both of France

[73] Assignee: Pharmindustrie, Gennevilliers, France

[21] Appl. No.: 360,150

[22] Filed: Mar. 22, 1982

[30] Foreign Application Priority Data

Apr. 3, 1981 [FR] France ................. 81 06713

[51] Int. Cl.³ .......................................... A61K 31/54
[52] U.S. Cl. ...................... 424/246; 544/42; 544/43; 544/44
[58] Field of Search ................. 544/42, 43, 44; 424/246

[56] References Cited

U.S. PATENT DOCUMENTS 2,909,521 10/1959 Jacob et al. ............. 544/42 X
2,931,810 4/1960 Yale et al. ............... 544/44 X
3,987,042 10/1976 Gueremy et al. .......... 544/43
4,155,874 5/1979 Nodiff et al. ............ 544/44 X

OTHER PUBLICATIONS

March, Advanced Organic Chemistry, McGraw-Hill (New York), 1977.

Primary Examiner—Richard Raymond
Attorney, Agent, or Firm—Beveridge, DeGrandi & Kline

[57] ABSTRACT

Compounds of the general formula:

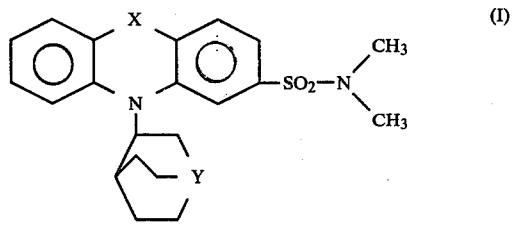

in which either X represents an atom of sulfur and Y represents the N-oxide group or X represents the sulfinyl group or the sulfonyl group and Y represents an atom of nitrogen or the N-oxide group and their salts of addition with mineral or organic acids, their process of preparation and their use as a medicament for the treatment of gastric and duodenal ulcers.

4 Claims, No Drawings

DERIVATIVES OF 10-(1-AZABICYCLO[2.2.2]OCT-3-YL)-N,N DIMETHYL-10H-PHENOTHIAZINE-2-SULFONAMIDE AS MEDICAMENTS

The present invention relates to new derivatives of 10(1-azabicylo[2.2.2]oct-3-yl)-N,N dimethyl-10H-phenothiazine-2 sulfonamide which can be used as medicaments or medicines, particularly in the treatment of gastric and duodenal ulcers.

These compounds may be represented by the following general formula:

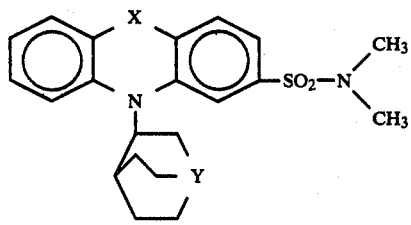

in which either X represents an atom of sulfur and Y represents the N-oxide group, or X represents the sulfinyl group or the sulfonyl group and Y represents an atom of nitrogen or the N-oxide group. In other words, X represents sulfur, sulfinyl or sulfonyl and Y represents nitrogen or N-oxide, with the proviso that when X is sulfur, Y is N-oxide.

When X represents the sulfinyl group, the molecule of the formula (I) compounds contains two asymmetrical centers; consequently, for a given significance of Y, there are two diastereoisomers corresponding to formula (I).

Each of these isomers, whether racemic or enantiomer, and mixtures thereof, form part of the invention in the same way as the salts resulting from the addition of these compounds to mineral or organic acids. Suitable mineral acids include hydrochloric acid, hydrobromic acid, sulfuric acid, nitric acid and phosphoric acid. Suitable organic acids include acetic acid, methanesulfonic acid, p-toluenesulfonic acid, fumaric acid, succinic acid, maleic acid and formic acid.

The formula (I) compounds for which X represents the sulfinyl or sulfonyl group and Y represents an atom of nitrogen may be prepared by oxidation of the compound of the formula:

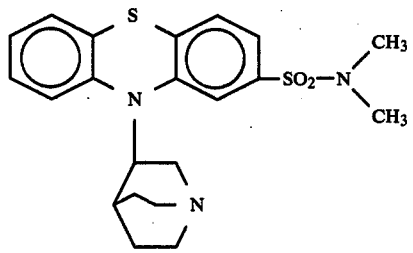

in the form of salts, preferably salts resulting from strong acids such as hydrochloric acid, sulfuric acid, methanesulfonic acid, or hydrobromic acid.

The oxidation is effected in accordance with methods which are known to the prior art and which enable a sulfide to be oxidized to sulfoxide or sulfone, for example, those described by J. March, Advanced Organic Chemistry, p. 1112, McGraw-Hill 1977. Useful methods consist of using as the oxidizing agent sodium metaperiodate in an aqueous medium or hydrogen peroxide in water and/or acetic acid at a temperature of between 20° and 100° C.

In order to obtain, preferentially, the formula (I) compounds in which X represents the sulfinyl group, it is of advantage to operate at a temperature of between 20° and 30° C. with sodium metaperiodate in an aqueous medium as the oxidizing agent.

In order to obtain, preferentially, the formula (I) compounds in which X represents the sulfonyl group, it is of advantage to operate at a temperature of between 50° and 100° C. in the presence of an excess of hydrogen peroxide in an aqueous, acetic acid or aqueous acetic acid medium.

The formula (I) compounds in which Y represents the N-oxide group may be prepared by oxidation of compounds of the formula:

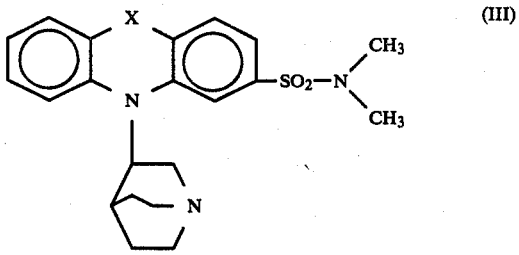

in which X has the same significance as in formula (I).

In order to carry out this oxidation, use is made of processes which are known to the prior art, for example, those described by J. March, Advanced Organic Chemistry p. 1111, McGraw-Hill 1977. The most usual method consists of heating the product to be oxidized to the boiling point in an alcohol solution of hydrogen peroxide.

The reaction mixtures which are obtained by the processes described above are treated in accordance with traditional methods (evaporation, extraction by means of a solvent, distillation, crystallization, chromatography etc.) in order to isolate the formula (I) compounds in the pure state.

The formula (I) compounds in the form of a free base may, if desired, be converted to salts of addition with a mineral acid or an organic acid by the action of such an acid in a suitable solvent.

The formula (II) compound may be prepared by means of the process described in British Pat. No. 1.492.157.

The following examples, which are not restrictive, illustrate the invention.

EXAMPLE 1

10-(1-azabicyclo[2.2.2]oct-3-yl)-N,N dimethyl-10H-phenothiaxine-2-sulfonamide S-oxide (mixture of the 2 diastereoisomers)

300 ml of water were added to 33 ml of an aqueous solution of 1.25 N methanesulfonic acid and then, while stirring, 17 g of 10-(1-azabicyclo[2.2.2]oct-3-yl)-N,N dimethyl-10H-phenothiaxine-2-sulfonamide were added. A solution of 9.2 g of sodium metaperiodate in 90 ml of water was added to the solution which was obtained.

Stirring took place for 48 hours at the ambient temperature. The solution was alkalized by means of concentrated ammonia and extracted 3 times with 200 ml of ethyl acetate. The organic phase was dried over magnesium sulfate and evaporated. The residue which was obtained was fixed on a column of silica and elution took place under pressure with a mixture of chloroform 50/diethylamine 10/hexane 40. In this way. 9.5 g of a mixture of diastereoisomers of 10-(1-azabicyclo[2.2.2]oct-3-yl)-N,N dimethyl-10H-phenothiaxine-2-sulfonamide S oxide were isolated. Analysis of the mixture by chromatography in the liquid phase showed that the percentage of each diastereoisomer was about 50%.

This mixture was put into solution in ethanol and converted, by adding an ethanol solution of hydrochloric acid, to its monohydrochloride which was recrystallized in a 95 ethanol/5 water mixture.

The compound which was obtained melted at 250° C. Analysis of the mixture by means of chromatography in the liquid phase showed that the percentage of each diastereoisomer was then 82% (form A) and 18% (form B).

EXAMPLE 2

10-(1-azabicyclo[2.2.2]oct-3-yl)-N,N dimethyl-10H-phenothiazine-2-sulfonamide S-oxide (Form A, pure)

One of the diastereoisomers (form A) was isolated from the mixture of the two 50/50 diastereoisomers prepared in accordance with Example 1 after a second chromatography under pressure with a mixture of chloroform 50/diethylamine 10/hexane 40.

This compound was converted in the ethanol into its monohydrochloride. After recrystallization in an ethanol 95/water 5 mixture, the product melted at 260° C.

EXAMPLE 3

10-(1-azabicyclo[2.2.2]oct-3-yl)-N,N dimethyl-10H-phenothiazine-2 sulfonamide S-dioxide A solution of 0.65 ml of methanesulfonic acid in 15 ml of acetic acid and finally a solution of 2.5 ml of 30% hydrogen peroxide in 5 ml of acetic acid were added slowly to a stirred solution of 4.1 g of 10-(1-azabicyclo[2.2.2]oct-3-yl)-N,N dimethyl-10H-phenothiazine-2-sulfonamide in 15 ml of acetic acid.

This mixture was heated to 60° C. while being stirred for 4 hours and then poured into 300 ml of water. Alkalization was effected by means of concentrated ammonia and then extraction took place twice with 100 ml of ethyl acetate. The organic phase was dried over magnesium sulfate and evaporated under reduced pressure. The residue obtained was fixed on a column of silica and elution took place under pressure with a chloroform 95/diethylamine 5 mixture In this way 3.72 g of 10-(1-azabicyclo[2.2.2]oct-3-yl)-N,N dimethyl-10H-phenothiazine-2-sulfonamide S-dioxide were isolated and this was converted in ethanol into its hydrochloride which melted at 250° C. after recrystallization in a 5/95 water-alcohol mixture.

EXAMPLE 4

10-(1-azabicyclo[2.2.2]oct-3-yl)-N,N dimethyl-10H-phenothiazine-2-sulfonamide N-oxide 2.4 ml of 31.5% hydrogen peroxide were added to a stirred solution of 8.3 g of 10-(1-azabicylco[2.2.2]oct-3-yl)-N,N dimethyl-10H-phenothiazine-2-sulfonamide in 100 ml of ethanol. Agitation under reflux took place for 4 hours. After cooling, 30 ml of saturated aqueous solution of sodium sulfite were added slowly in order to destroy the excess peroxides. The solvents were evaporated under reduced pressure, the residue was made up with water and brought to pH 12 by the addition of a concentrated solution of sodium hydroxide. The aqueous phase was extracted twice with 20 ml of chloroform; the organic extracts were dried over magnesium sulfate and evaporated under reduced pressure.

The residue obtained was fixed on a column of silica and was eluted under pressure with a mixture of ethyl acetate 14/methanol 4/diethylamine 3. In this way, 8 g of 10-(1-azabicyclo[2.2.2]oct-3-yl)-N,N dimethyl-10H-phenothiazine-2-sulfonamide N-oxide were obtained and were converted in acetone, by the addition of hydrochloric ether, to its hydrochloride which melted at 245° C.

EXAMPLE 5

10-(1-azabicyclo[2.2.2]oct-3-yl)-N,N dimethyl-10H-phenothiazine-2-sulfonamide S-oxide N-oxide 1.3 ml of a 31% solution of hydrogen peroxide were added to a solution of 4.8 g of 10(1-azabicyclo[2.2.2]oct-3-yl)-N,N dimethyl-10H-phenothiazine-2-sulfonamide S-oxide prepared in accordance with Example 1 in 60 ml of ethanol. Agitation under reflux took place for 48 hours. After cooling, 30 ml of a saturated aqueous solution of sodium sulfite were added in order to destroy the excess peroxides. The solvents were evaporated under reduced pressure, and the residue was made up with water and brought to pH 12 by the addition of a concentrated solution of sodium hydroxide.

The aqueous phase was extracted twice with 20 ml of chloroform; the organic extracts were then dried over magnesium sulfate and evaporated under reduced pressure. The residue obtained was fixed on a column of silica and elution took place with a mixture of ethyl acetate 14/methanol 4/diethylamine 3.

In this way, 1 g of a mixture of the two diastereoisomers of 10-(1-azabicyclo[2.2.2]oct-3-yl)-N,N dimethyl-10H-phenothiazine-2-sulfonamide S-oxide N-oxide was obtained which melted at about 130° C.

Pharmacological Properties

The antisecretory activity of the compounds in accordance with the formula (I) invention has been studied on the gastric hypersecretion stimulated by pentagastrine in dogs wearing a Heidenhain pouch.

Experimental Procedure

Three mongrel dogs wearing Heidenhain pouches and which were kept without food for 18 hours received a venous perfusion of 4 mg per kg of pentagastrine per hour in a volume of 30 mls per hour for 4 hours. The secretion from the pouch was collected in a flask which was changed every 15 minutes. An hour and a half after the beginning of the perfusion process, the product to be examined was administered orally in a No. 000 gelatin coated pill. The 50% effective dose (ED 50) is the dose which reduced by 50% the hourly acid flow at the 3rd or 4th hour of the experiments in relation to the acid flow at the second hour of the perfusion. The doses are expressed in the product in the base form. The results were as follows:

| Products | ED 50 in mg/kg po |
| --- | --- |
| Cimetidine | 2.3 |
| Example 1 | 2.3 |
| Example 2 | 2.5 |
| Example 3 | 10 |

The products of the invention are, therefore, powerful inhibitors of gastric secretion. In particular, the products of Examples 1 and 2 are as active as Cimetidine.

Toxicological Properties

The acute toxicities of the compounds in accordance with the invention were determined on $CD_1$ male mice (Charles RIVER) by oral administration. The $LD_{50}$'s were calculated after 3 days' observation by the cumulative method of J. J. Reed and H. Muench (Amer. J. Hyg. 1938, 27, 493).

The compounds behave as substances of a relatively low toxicity in mice since the $LD_{50}$'s of the compounds are between 500 and 1000 mg/kg/

Therapeutic Use

The compounds in accordance with the invention and their pharmaceutically acceptable salts can be used in human therapy in the form of tablets, capsules, gelatin coated capsules, suppositories, ingestible or injectable solutions etc., as inhibitors of gastric secretion for the treatment of duodenal and gastric ulcers.

The posology depends on the effects desired and the manner of administration used. For example, when administered orally, it can be between 50 and 500 mg of active substance per day with unit doses of between 10 and 100 mg.

What is claimed is:

1. A process for treating a human suffering from duodenal and gastric ulcers which comprises orally administering to said human 50 to 500 mg per day of a compound of the formula

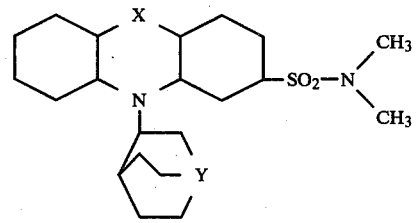

in which either X represents an atom of sulfur and Y represents the N-oxide group, or X represents the sulfinyl group or the sulfonyl group and Y represents an atom of nitrogen or the N-oxide group, or its salt of addition with a pharmaceutically acceptable acid.

2. The process according to claim 1 wherein the compound is administered in the form of a tablet, capsule, gelatin coated capsule, suppository or injestible or injectable solution.

3. The process according to claim 1 wherein in said compound X represents the sulfinyl group and Y represents an atom of nitrogen or the N-oxide group in the form of their racemic or enantiomer diastereoisomers.

4. The process according to claim 3 wherein the compound is administered in the form of a tablet, capsule, gelatin coated capsule, suppository or injestible or injectable solution.

* * * * *